United States Patent [19]

Rupinskas

[11] 4,424,249

[45] Jan. 3, 1984

[54] SPONGE FABRIC

[75] Inventor: Vytautas R. Rupinskas, Lombard, Ill.

[73] Assignee: The Kendall Company, Boston, Mass.

[21] Appl. No.: 461,352

[22] Filed: Jan. 27, 1983

[51] Int. Cl.³ .............................................. B32B 3/00
[52] U.S. Cl. .................................... 428/195; 428/296
[58] Field of Search ............... 428/195, 198, 296, 171, 428/172

[56] References Cited

U.S. PATENT DOCUMENTS 3,672,949  6/1972  Brown ................................ 428/198
3,687,797  8/1972  Wideman ........................... 428/198
4,142,334  3/1979  Hirsch et al. ....................... 428/195

Primary Examiner—James J. Bell
Attorney, Agent, or Firm—Powell L. Sprunger

[57] ABSTRACT

A sponge fabric comprising, a nonwoven material in sheet form having a mass of randomy disposed fibers. The sheet has a bonding pattern in the form of a plurality of diamonds, with each of the diamonds in the pattern having a plurality of sides and being free of corners, and with each side of a specified diamond in the pattern being the side of an adjacent diamond.

15 Claims, 3 Drawing Figures

SPONGE FABRIC

BACKGROUND OF THE INVENTION

The present invention relates to sponge fabrics. Presently, sponge fabrics are placed over a wound of a patient, and a combine dressing, such as an abdominal pad, is placed over the sponge fabric. Present sponge fabrics result in horizontal flow of exudate from the wound along the fabric to a location around the wound which is undesired, since the exudate may result in irritability and maceration around the wound and resulting in possible infection. It is desired that the exudate flow vertically through the fabric directly into the dressing. However, in order to achieve this result, it is desired that stiffness is not imparted to the fabric which would impede the hand of the fabric.

SUMMARY OF THE INVENTION

A principal feature of the present invention is the provision of an improved sponge fabric of simplified construction.

The sponge fabric of the present invention comprises, a nonwoven material in sheet form having a mass of randomly disposed fibers. The sheet has a bonding pattern in the form of a plurality of diamonds, with each of the diamonds in the pattern having a plurality of sides and being free of corners, and with each of a specified diamond in the pattern being the side of an adjacent diamond.

A feature of the present invention is that the pattern retards horizontal flow of exudate through the fabric.

Another feature of the invention is that the pattern enhances the vertical flow of exudate through the fabric.

Still another feature of the invention is that the pattern is free of corners, i.e., has gaps, such that the pattern does not significantly impair the hand of the fabric and impart an undesired stiffness to the fabric.

Further features will become more fully apparent in the following description of the embodiments of this invention and from the appended claims.

DESCRIPTION OF THE PREFERRED EMBODIMENTS

Figure 1:
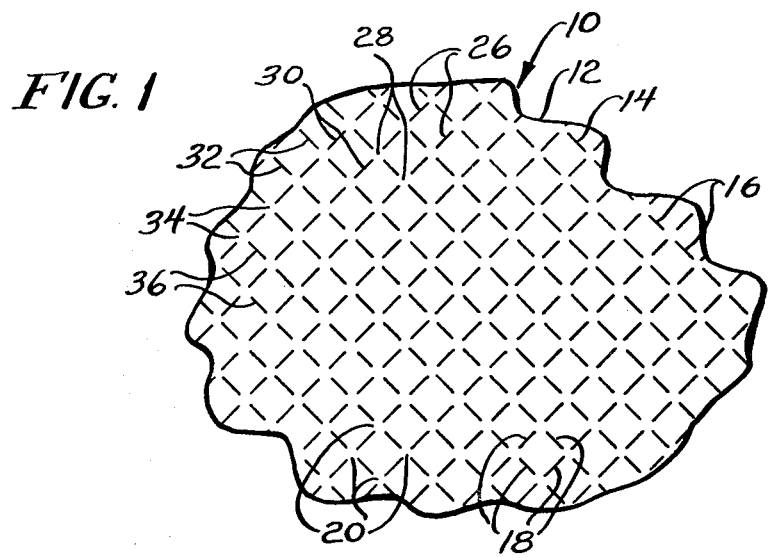
FIG. 1 is a fragmentary plan view of a sponge fabric of the present invention.

Referring now to FIG. 1, there is shown a sponge fabric generally designated 10, comprising a nonwoven material in the form of a sheet 12 having a mass of randomly disposed fibers in the sheet 12. As shown, the sheet 12 has a bonding pattern 14 in the form of a plurality of diamonds 16. Each of the diamonds 16 in the pattern 14 has four sides 18, and is free of four corners 20, i.e., has gaps, at the ends of the sides 18. Also, as shown, each side 18 of a specified diamond in the pattern 14 is the side 18 of an adjacent diamond 16 in the pattern 14.

As an alternative explanation, the pattern 14 has a plurality of spaced first parallel lines 26 having gaps 28 defining a plurality of spaced line segments 30 in the first lines 26, and a plurality of spaced second parallel lines 32 generally perpendicular to the first lines 26 and having gaps 34 defining a plurality of spaced line segments 36 in the second lines 32. As shown, the length of the segments 30 and 36 and gaps 28 and 34 of the first and second lines 26 and 32, respectively, is approximately equal, and the gaps 34 of the second lines 32 are located in the gaps 28 of the first lines 26.

In one form, the sheet 12 may comprise entirely thermoplastic fibers, such as polyester, polypropylene, acrylic, or nylon, and the bonding pattern 14 is heat bonded on the fabric 10. Alternatively, the sheet 12 may comprise entirely cellulosic fibers, such as rayon or cotton, and the bonding pattern 14 is print bonded on the fabric 10, such as by a hydrophobic material which extends through the fabric. Further, the sheet 12 may comprise a mixture of thermoplastic fibers and cellulosic fibers, in which case the bonding pattern 14 is either heat bonded or print bonded on the fabric 10.

Figure 2:
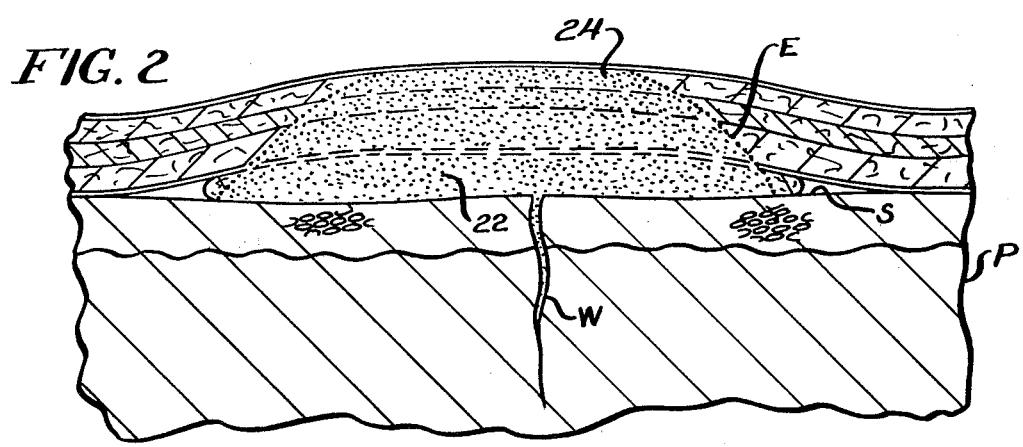
FIG. 2 is a fragmentary sectional view showing a sponge fabric of the prior art and a combine dressing over a wound of a patient.

Referring to FIG. 2, a sponge fabric 22 of the prior art is shown in place over a wound W of a patient P, and a combine dressing 24, such as an abdominal pad, is illustrated in place over the fabric 22. As shown, the exudate E from the wound W spreads horizontally through the fabric 22 to a location around the wound against the skin S, and also spreads into the dressing 24 at a location around the wound W. In this form, the exudate around the wound W may result in irritability and maceration around the wound W which may result in possible infection.

Figure 3:
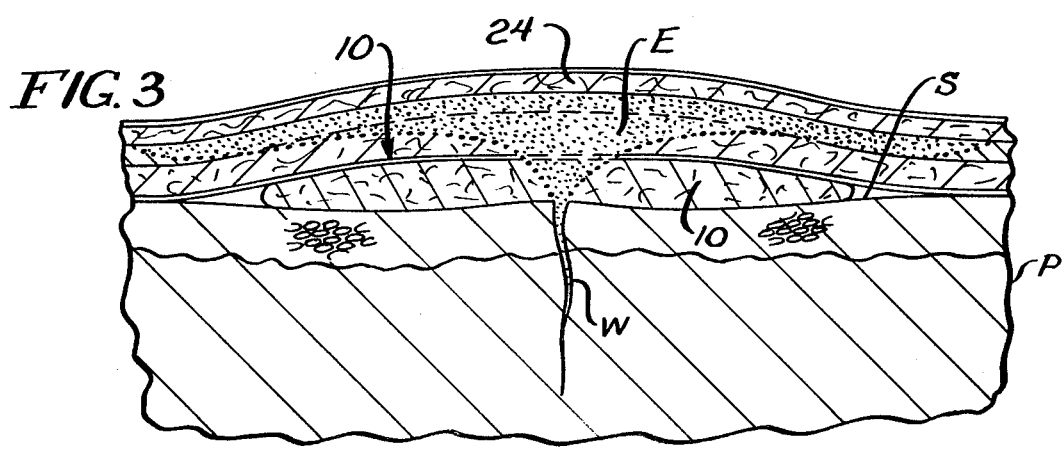
FIG. 3 is a fragmentary sectional view illustrating the sponge fabric of the present invention and a combine dressing over a wound of the patient.

In contrast, with reference to FIG. 3, there is shown one or more plies of the fabric 10 of the present invention in place over the wound W, and a dressing 24 in place over the fabric 10. As shown, the exudate E from the wound W flows substantially directly vertically through the fabric 10 into the dressing 24 where it is captured for retention therein. Thus, the pattern in the sponge fabric 10 of the present invention minimizes the horizontal flow of exudate E through the fabric 10 in order to prevent collection of exudate in the fabric 10 around the wound W. Also, the pattern 14 of the fabric 10 is free of corners in the diamonds 16, such that the hand is not impaired which otherwise would result in undesired stiffness of the fabric 10.

The foregoing detailed description is given for clearness of understanding only, and no unnecessary limitations should be understood therefrom, as modifications will be obvious to those skilled in the art.

I claim:

1. A sponge fabric, comprising a nonwoven material in sheet form having a mass of randomly disposed fibers, said sheet having a bonding pattern in the form of a plurality of diamonds, with each of the diamonds in the pattern having a plurality of sides and being free of corners, and with each side of a specified diamond in the pattern being the side of an adjacent diamond.

2. The fabric of claim 1 wherein each diamond in the pattern has four sides, and in which each diamond is free of four corners.

3. The fabric of claim 1 wherein the sheet comprises entirely thermoplastic fibers, and in which the bonding pattern is heat bonded on the fabric.

4. The fabric of claim 1 wherein the sheet comprises a mixture of thermoplastic and cellulosic fibers.

5. The fabric of claim 4 wherein the bonding pattern is print bonded on the fabric.

6. The fabric of claim 4 wherein the bonding pattern is heat bonded on the fabric.

7. The fabric of claim 1 wherein the sheet comprises entirely cellulosic fibers, and in which the bonding pattern is print bonded on the fabric.

8. A sponge fabric, comprising a nonwoven material in sheet form having a mass of randomly disposed fibers, the sheet having a bonding pattern in the form of a plurality of spaced first parallel lines having gaps defining a plurality of spaced line segments in the first lines, and a plurality of spaced second parallel lines disposed at an angle to the first lines and having gaps defining a plurality of spaced line segments in the second lines, with the gaps of the second lines being located in the gaps of the first lines.

9. The fabric of claim 8 wherein the length of the line segments and gaps in the first and second lines is approximately equal.

10. The fabric of claim 8 wherein the second lines are approximately perpendicular to the first lines.

11. The fabric of claim 8 wherein the sheet comprises entirely thermoplastic fibers, and in which the bonding pattern is heat bonded on the fabric.

12. The fabric of claim 8 wherein the sheet comprises a mixture of thermoplastic and cellulosic fibers.

13. The fabric of claim 12 wherein the bonding pattern is print bonded on the fabric.

14. The fabric of claim 12 wherein the bonding pattern is heat bonded on the fabric.

15. The fabric of claim 8 wherein the sheet comprises entirely cellulosic fibers, and in which the bonding pattern is print bonded on the fabric.

* * * * *